United States Patent [19]

Ramachandran et al.

[11] Patent Number: 5,008,414
[45] Date of Patent: Apr. 16, 1991

[54] PROCESS FOR THE PRODUCTION OF OXIDES

[75] Inventors: Ramakrishnan Ramachandran, Allendale; Donald L. MacLean, Annandale; Donald P. Satchell, Jr., Summit; Virginia A. Malik, Linden, all of N.J.

[73] Assignee: The BOC Group, Inc., Murray Hill, N.J.

[21] Appl. No.: 410,435

[22] Filed: Sep. 21, 1989

Related U.S. Application Data

[63] Continuation-in-part of Ser. No. 281,581, Dec. 8, 1988, Pat. No.

[51] Int. Cl.$^5$ ............... C07D 301/10; C07D 301/08; C07D 301/32
[52] U.S. Cl. .................................... 549/538; 549/523; 549/532; 549/534; 549/535; 549/536
[58] Field of Search ............... 549/523, 534, 535, 536, 549/532, 538

[56] References Cited

U.S. PATENT DOCUMENTS

| | | | |
|---|---|---|---|
| 3,176,444 | 4/1965 | Kiyonaga | 55/26 |
| 4,498,910 | 2/1985 | Benkmann | 55/18 |
| 4,609,502 | 9/1986 | Khoobtar | 558/319 X |
| 4,754,059 | 6/1988 | Khoobtar | 558/320 |
| 4,849,538 | 7/1989 | Ramachandran et al. | 558/319 |
| 4,868,330 | 9/1989 | Ramachandran et al. | 558/319 X |
| 4,870,201 | 9/1989 | Ramachandran et al. | 558/319 |

OTHER PUBLICATIONS

Solomons, "Organic Chemistry", p. 212, (1978), John Wiley & Sons.

Primary Examiner—Joseph Paul Brust
Attorney, Agent, or Firm—Carol A. Nemetz; Robert I. Pearlman

[57] ABSTRACT

An improved process is provided for the production of oxides from hydrocarbons by reaction with oxygen, air or a gas enriched in oxygen relative to air, preferably the latter in the presence of an oxidation catalyst. An alkane, e.g. propane, is converted to an alkene in a catalytic dehydrogenator. The product stream is introduced into an oxidation reactor. The product formed therein is recovered in a conventional quench tower. The gaseous effluent from the quench tower is treated in a separator to produce an adsorbed stream, an oxygen-enriched stream, a waste stream and, if desired, a hydrogen-enriched stream. The oxygen-enriched stream may be recycled to the oxidation reactor depending on the nitrogen content thereof. The adsorbed stream plus at least a portion of the hydrogen-enriched stream is introduced into a selective oxidation unit to remove the remaining oxygen and then recycled to the dehydrogenator. The remainder of the hydrogen-enriched stream, if any, may be taken as product or vented. The dehydrogenator may be a multistage dehydrogenator wherein the product stream is withdrawn from a reactor other than the first and last reactors, the recycle streams are introduced into the next sequential reactor and the effluent from the last reactor is introduced into the first reactor, a reactor having a similar alkane composition or directly into the oxidation reactor.

27 Claims, 7 Drawing Sheets

PROCESS FOR THE PRODUCTION OF OXIDES

RELATED APPLICATIONS

This application is a divisional of U.S. patent application Ser. No. 7/281,581, filed Dec. 8, 1988 and now U.S. Pat. No. 4,870,201 issued Sept. 26, 1989.

TECHNICAL FIELD

The present invention is directed to an improvement in a process for producing alkylene oxides from alkanes and an oxygen-containing gas in the presence of a suitable catalyst under conditions which achieve high efficiency and selectivity toward the desired product.

BACKGROUND OF THE INVENTION

The production of oxides by oxidation of an appropriate alkane in the presence of suitable catalyst is well known.

Brian J. Ozero, *Handbook of Chemicals Production Processes*, edited by Robert Meyers, McGraw Hill Book Co. (1986) at Chapter 1.5, discusses cyclic processes using both oxygen and air as oxidant for the production of ethylene oxide (EO) from ethylene. In these processes, the alkene is oxidized in a multitubular catalytic reactor in vapor phase. The reactor off gases are cooled and scrubbed with water in an absorber to recover ethylene oxide which is sent to the recovery section for further purification.

In the oxygen-based process described by Ozero, the scrubber off gases are divided into three parts which are: i) recycled to the reactor, ii) vented and iii) sent to a separator for carbon dioxide removal and recycle of the remaining hydrocarbons. This process suffers from several disadvantages. For example, the oxygen-based ethylene oxide process requires a separate carbon dioxide removal unit and a purge to remove argon to prevent its accumulation.

In the air-based process described by Ozero, the scrubber off gases are sent to a second reactor, which is the purge reactor, where additional unreacted ethylene is reacted using a higher air to ethylene ratio, foregoing some EO selectivity. The reactor off gases are again passed through another water scrubber to recover EO produced. It is known that the volume of hydrocarbons purged, when utilizing air as a source of oxygen, requires that the purge scrubber off gases be incinerated to remove any remaining hydrocarbons in order to meet environmental regulations. In this air-based process, an additional purge oxidation reactor, a water scrubber, and an effluent incinerator are required, as well as a greater volume of catalyst. Also, both this and the oxygen-based process use the expensive ethylene as the raw material. The processes described by Ozero are limited to either pure oxygen or air.

Khoobiar et al.. U.S. Pat. No. 4,609,502, discloses a cyclic process for producing acrylonitrile using propane as a starting material. This process differs from the production of oxides by the presence of ammonia and the choice of catalyst. In the process disclosed by Khoobiar et al., the alkane is initially dehydrogenated catalytically in the presence of steam to form propylene. This is in contrast to most conventional dehydrogenation processes which avoid steam primarily due to the costs involved. After ammoxidation, the effluent is quenched to remove the desired product, and the off-gases, including propylene and propane, are sent to an oxidation reactor to remove oxygen by selective reaction with hydrogen to form water vapor. The gas mixture exiting the selective oxidation reactor includes substantial amounts of methane, ethane and ethylene, which are byproducts of dehydrogenation, and unreacted propylene and propane, in addition to carbon oxides. A sufficient portion of this gas mixture is purged to remove the net production of carbon oxides and light hydrocarbons.

Optionally, this gas mixture is split and a portion sent to a separator which removes only carbon dioxide. A portion of the effluent from the separator is purged to remove light hydrocarbons. The nonpurged portion is mixed with the remainder of the oxidation reactor effluent, fresh propane, and steam, if necessary. This mixture is sent to the dehydrogenator where the propane is converted to propylene. Another option is to cool and liquefy the $C_3$ hydrocarbons from the oxidation reactor, and then vaporize the hydrocarbons prior to recycle.

In the process disclosed by Khoobiar et al., there is no practical way to remove byproducts of propane dehydrogenation, such as methane, ethane, ethylene and the like, thereby preventing their accumulation in the system, other than by removing them in a purge stream. The removal of these gases in a purge stream will likewise result in a loss of the circulating propane and propylene, thus causing a significant decrease in the overall yield of propylene to acrylonitrile. While, as mentioned above, propane and propylene can be recovered from the stream prior to venting, this requires additional refrigeration apparatus to cool and liquefy the propylene and propane. The separated $C_3$ hydrocarbons must be vaporized prior to recycle. These operations add to the capital and power requirements of the process.

Another disadvantage of the Khoobiar et al. process stems from the use of the selective oxidation reactor to treat the gaseous effluent exiting the quench tower. This quench effluent is at ambient temperature and must be heated prior to introduction into the oxidation reactor in order to promote oxygen removal. Because there is a significant amount of oxygen in the quench effluent, the heat of reaction generated in the oxidation reactor can result in excessive temperatures in the system. There are three know methods to alleviate this problem. First, the amount of oxygen entering the oxidation reactor can be reduced by other means. Second, multiple reactors can be utilized with a cooling means between each pair of reactors. Third, a portion of the oxidation reactor can be passed through a cooling means and recycled to the feed to reduce the internal temperature of the reactor. None of these measures is attractive from the viewpoint of cost and efficiency.

The oxidation reactor in the Khoobiar et al. process is operated with oxidation catalysts such as noble metals (e.g., platinum). Olefins and carbon monoxide, which are generated in the dehydrogenation reactor, are known to deactivate these catalysts, as disclosed in Charles L. Thomas, *Catalytic Processes and Proven Catalysts*, Academic Press (1970) at 118-119. Accordingly, multiple oxidation reactors must be used (see Khoobiar et al. at column 4, lines 51-56) to allow for frequent regeneration of the catalyst which represents yet another addition to production costs. These consideration apply as well to the catalytic production of oxides from alkanes as contemplated herein.

It is therefore apparent that the industry is still searching for a cost effective process of converting alkanes into oxides The process of the present invention is cost effective and substantially reduces or eliminates disadvantages of the aforementioned systems Moreover, in comparison to conventional processes, the thermal requirements of the present invention process are markedly reduced.

SUMMARY OF THE INVENTION

A process is disclosed for the production of alkylene oxides comprising converting a gaseous alkane to the corresponding alkene in a dehydrogenator, reacting the alkene in an oxidation reactor with an oxygen-containing gas, preferably oxygen-enriched air, in the presence of an oxidation catalyst to form the desired oxide. The product stream is quenched with a liquid to form a liquid phase containing the desired product and a gas phase which is passed under pressure into a separator which provides an oxygen-enriched stream, a recycle stream comprising reactant alkane and alkene hydrocarbons, and a waste stream comprising carbon dioxide and lower hydrocarbons which may be vented or otherwise discarded. A hydrogen-enriched stream may also be produced if desired. Nitrogen, when present in the feed stream, is removed in the oxygen-enriched stream. The recycle stream is passed into a selective oxidation unit where minor amounts of residual oxygen are removed. The effluent from the selective oxidation unit is recycled to the dehydrogenator with fresh alkane feed. The oxygen-enriched stream from the separator may be recycled to the oxidation reactor, depending on the nitrogen content thereof. In one embodiment of the present invention, the separator system produces a hydrogen-enriched stream which may be recycled to the dehydrogenator, the selective oxidation unit or withdrawn as product. The dehydrogenator may be a single unit or a multistage unit wherein the recycle stream is admitted to a particular stage following that from which the effluent for the reactor is withdrawn. A second separator may be present between the dehydrogenator and the oxidation reactor to remove hydrogen from the dehydrogenator effluent. When the second separator is present, the first separator does not produce a hydrogen-enriched stream. Each separator may be one or more separation units known to those skilled in the art, e.g., absorber, cryogenic setup, membrane or pressure swing adsorber (PSA). Note that while streams are designated with respect to certain compositions of interest, the streams will contain others at least in trace amounts, which do not affect operation of the process of the present invention. For example, carbon dioxide will be present in the recycle hydrocarbon stream.

DESCRIPTION OF THE PREFERRED EMBODIMENTS

The process of this invention is applicable to the synthesis of alkylene oxides. In each instance, an alkene is reacted with an oxygen-containing gas comprising pure oxygen, or a gas enriched in oxygen relative to air, in the presence of a suitable catalyst. The term "suitable catalyst" indicates a catalyst that will catalyze the production of the desired product, e.g. ethylene oxide from ethylene or propylene oxide from propylene, under the conditions utilized in the reactor that is, an oxirane ring or alkylene oxide will be formed.

In the interest of brevity, the subject process will be described with reference to the production of propylene oxide from propane, but is in no way intended to be limited thereto.

Figure 1:
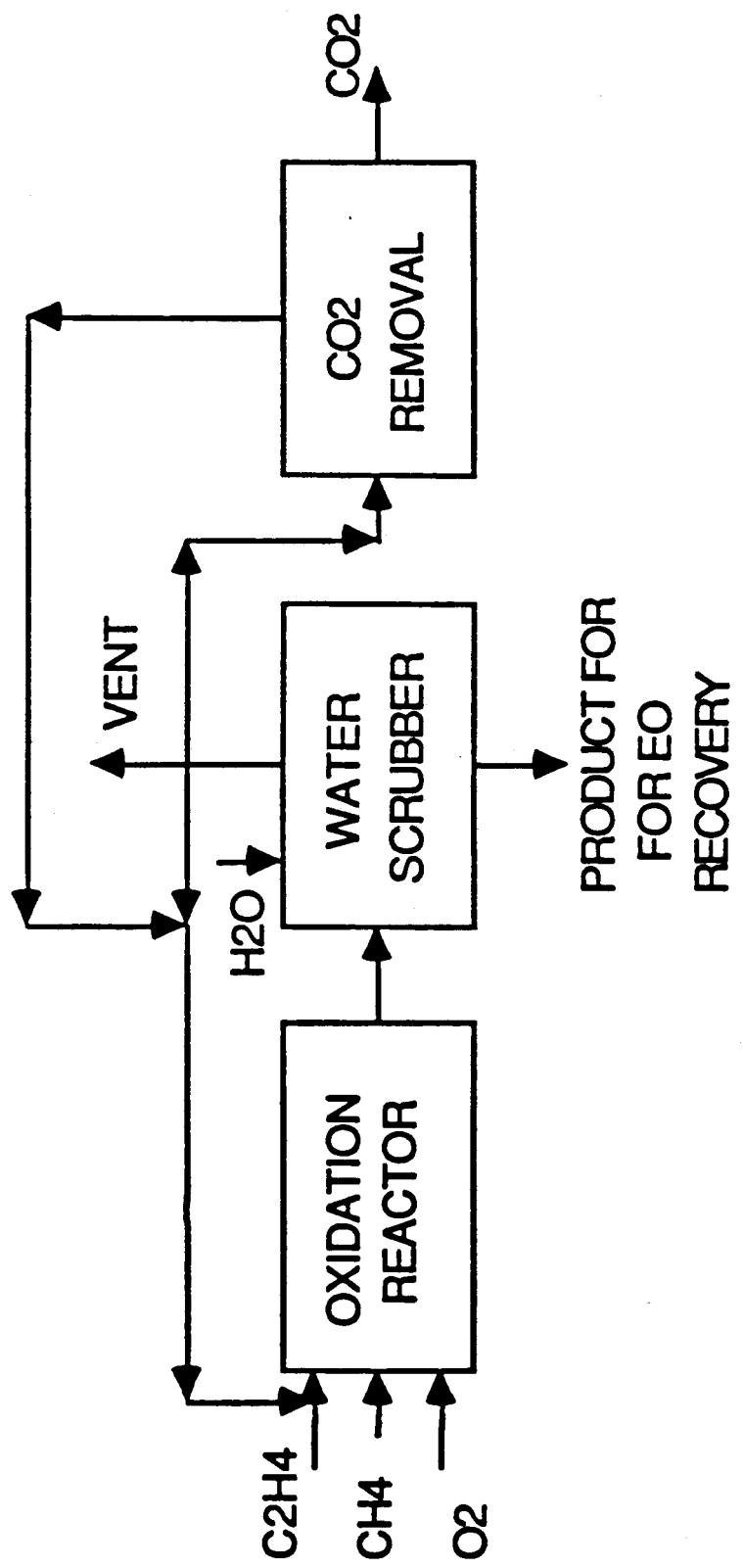
FIG. 1 illustrates in a block diagram a present conventional process of producing ethylene oxide using oxygen.
Figure 2:
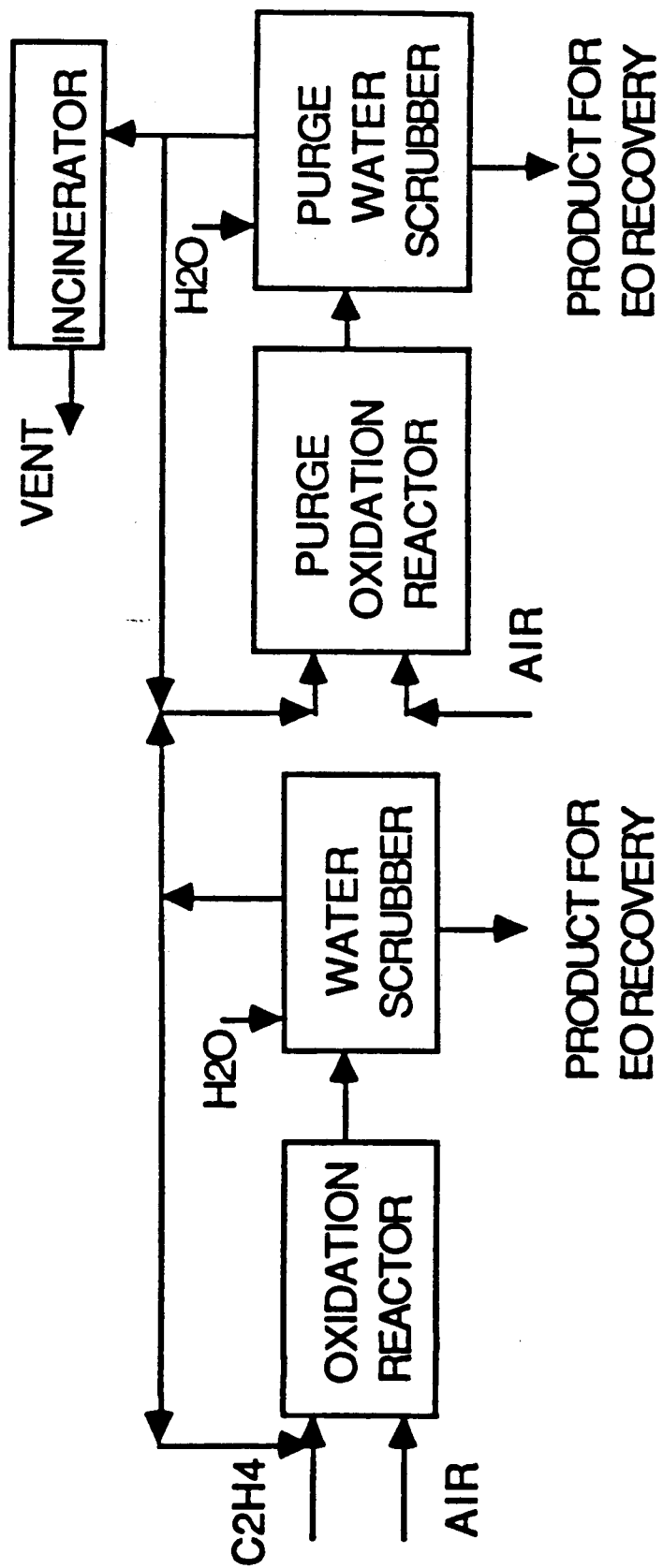
FIG. 2 illustrates in a block diagram a present conventional process of producing ethylene oxide using air.

Turning to the drawings, a process currently utilized commercially to produce oxides such as ethylene oxide, is illustrated in FIGS. 1 and 2. In FIG. 1, ethylene and oxygen are fed into a conventional reactor containing a suitable oxidation catalyst; in FIG. 2, ethylene and air are similarly fed. The reactor may be of any conventional fixed or fluidized bed design, typically the former. Such processes typically employ a recycle step to increase the overall process efficiency. The oxygen concentration in the feed to the reactor is adjusted to maximize the selectivity to the desired product.

In the oxygen-based process, shown in FIG. 1, methane is added continuously to the reactor as a flame suppressor to compensate for the loss in the purge. The oxidation reactor off gases are sent to a water scrubber to remove products for ethylene oxide recovery. The scrubber off gases are divided into three parts: a first part is recycled back to the reactor, a second part is vented, and a third part is sent to a $CO_2$ removal unit. After removing $CO_2$, the off gases of the third part are sent back to the reactor. The purge is essential to prevent any argon build up in the system. Since there is no other way to remove inerts from the system, one cannot use air or oxygen-enriched air as the oxidant feed since the large volume required to purge the nitrogen would cause excessive loss of feed hydrocarbon, ethylene.

In the air-based process, shown in FIG. 2, ethylene and air are fed into the oxidation reactor. The reactor products are water scrubbed to remove the ethylene oxide produced. A part of the scrubber off gases are recycled back to the reactor while the remainder is sent to a second reactor. Additional air is added to this second reactor to achieve an air-to-ethylene feed ratio higher than the first reactor so that a high ethylene conversion is obtained. The off gases of the second reactor are sent to a second water scrubber to remove and recover the additional ethylene oxide produced. The second scrubber off gases are split into two portions—one is recycled back to the first oxidation reactor while the other is purged, typically via incineration.

Figure 3:
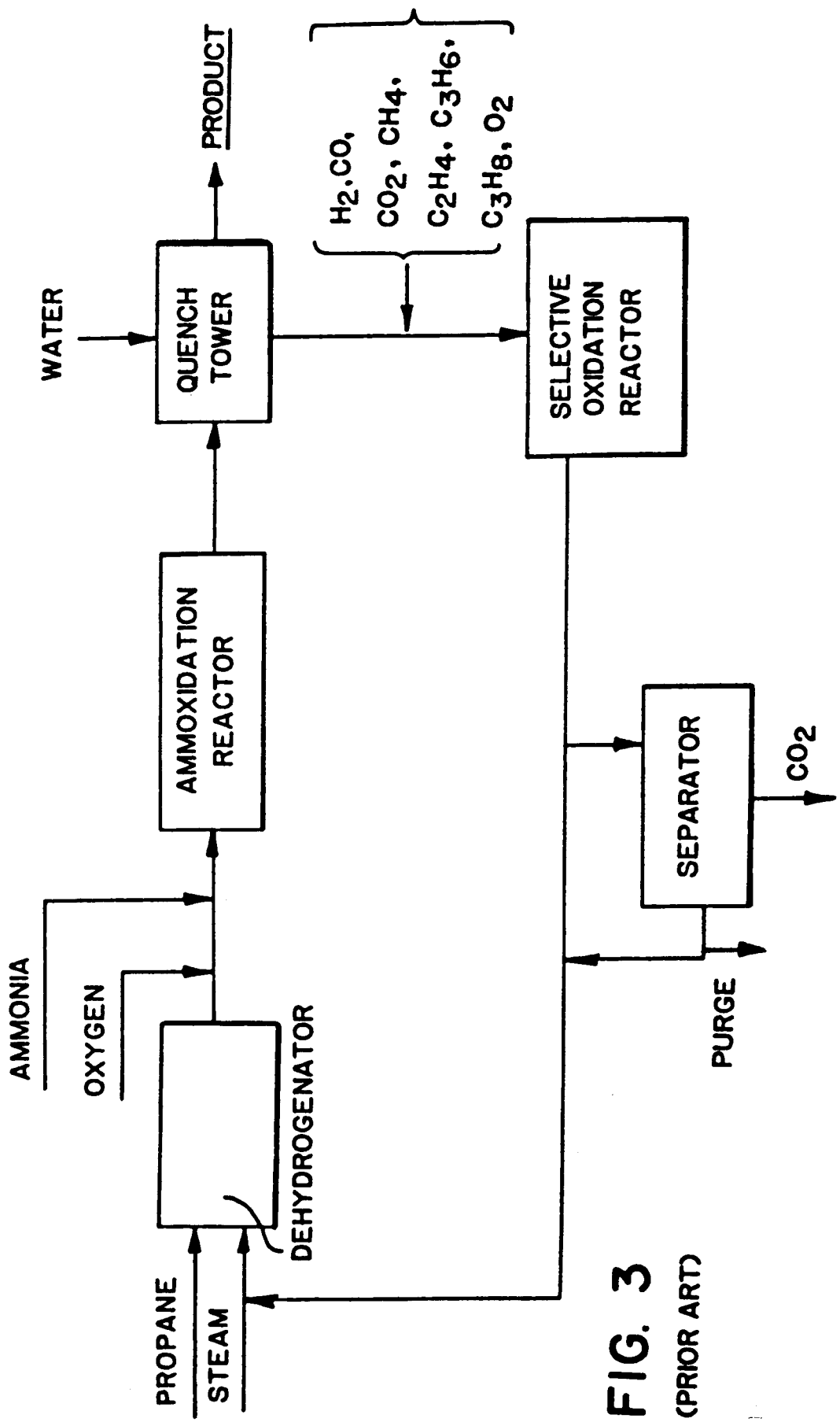
FIG. 3 illustrates in a block diagram a present conventional process of producing acrylonitrile utilizing a recycle step.

FIG. 3 illustrates the cyclic process for producing acrylonitrile disclosed in Khoobiar et al., U.S. Pat. No. 4,609,502. In this process, propane and steam are fed into a dehydrogenator to form propylene, which is then mixed with oxygen and ammonia and fed into an ammoxidation reactor such as described in FIG. 1. The product of the reactor is fed to an aqueous quench tower as in FIG. 1 and the products withdrawn in solution. The gaseous off gases from the quench tower, typically containing oxygen, hydrogen, carbon monoxide, carbon dioxide, methane, ethane, ethylene, propane and propylene, is fed to a selective oxidation reactor. It is generally essential for the efficient operation of such a reactor to heat the gas mixture prior to introduction therein.

A portion of the off gas from the oxidation reactor is passed to a separator to remove carbon dioxide by an undisclosed mechanism. A portion of the separator effluent, which contains light hydrocarbons and hydrogen, is purged, treated to remove propane and propylene (not shown) and then discarded, thereby preventing buildup of by products in the system. The propane and propylene are combined not shown with the remainder of the selective oxidator effluent and the remainder of the separator effluent and recycled to the dehydrogenator. It is, of course, necessary for the selective oxidation reactor to be effective in removing all oxygen from the quench tower effluent to prevent significant loss of effectiveness of the dehydrogenator. It is also necessary for the oxygen feed to be pure oxygen since the use of air or oxygen-enriched air would produce a rapid accumulation of nitrogen in the system. This would, in turn, require the purging of a larger portion of the recycle stream with resulting loss of efficiency.

Figure 4:
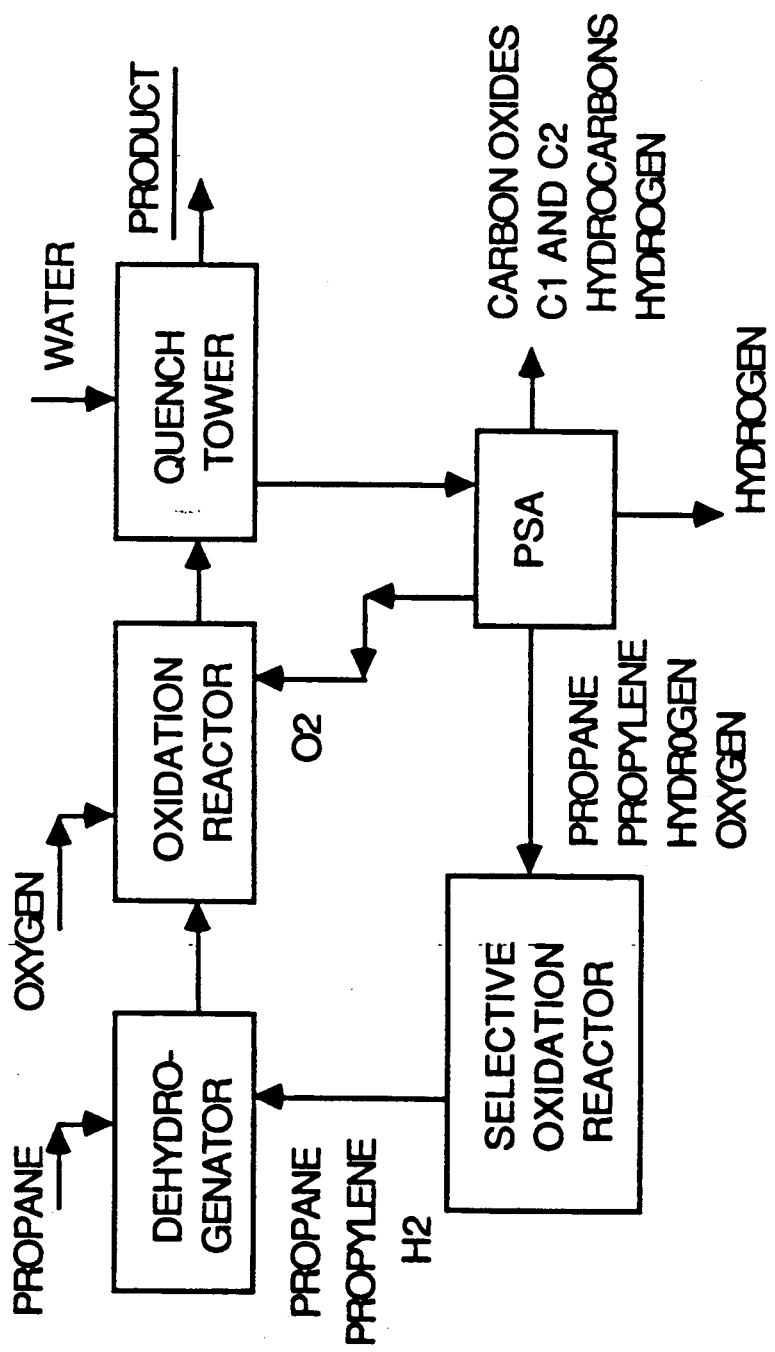
FIG. 4 illustrates in a block diagram the improvement of the present invention in a process for producing propylene oxide wherein a selective oxidation unit is downstream of the PSA system.

The cyclic process for producing alkylene oxides provided in accordance with the present invention is illustrated in FIG. 4 The process shown in FIG. 4 provides the efficiency of recycle afforded by the process illustrated in FIG. 3 but is substantially more efficient and, unexpectedly, capable of effectively utilizing oxygen-enriched air as a feed to the oxidation reactor. Specifically, one embodiment of the subject process utilizes a PSA system having an operating cycle such that it will produce an oxygen-enriched stream which will also contain nitrogen, if present in the feed stream, a recycle stream containing unreacted alkane/alkene hydrocarbons from the quench tower effluent, a waste stream containing hydrogen, carbon oxides and lower hydrocarbons and a hydrogen-enriched stream. These streams can be recycled to the oxidation reactor, the dehydrogenator or the selective oxidation unit, as appropriate. Since the recycle stream contains only a small quantity, i.e. typically 1 to 2 percent by volume of oxygen, the selective oxidation reactor can be comparatively small in terms of capital expenditure and have a long life, yet still function effectively. The configuration of the subject process eliminates the substantial loss of efficiency inherent in the process of FIG. 3 by the use of the purge stream. This recycle stream may also contain hydrogen. In addition, the novel operation of the PSA system of the subject invention provides for recycle of an oxygen-enriched stream, thus providing a further increase in process efficiency. The hydrogen-enriched stream may be recycled as well or withdrawn as product.

Referring to FIG. 4, propane is fed into the dehydrogenator where it is converted to propylene. For increased catalyst life, a hydrogen-containing gas may be introduced into the dehydrogenator with the propane feed. The required amount of hydrogen can conveniently be provided through the recycle stream from the PSA system as will be discussed below. The hydrogen-containing gas can, if desired, be provided as a discrete stream. The dehydrogenator can be of any design including a multistage dehydehydrogenator, as will be discussed hereafter. The catalyst utilized in the dehydrogenator can be any conventional dehydrogenation catalyst, preferably one or more Group VIII noble metals such as platinum on an alumina support. A steam-assisted dehydrogenator may be utilized as well but with some loss in performance.

The effluent stream from the dehydrogenator, comprising unreacted propane, propylene and hydrogen, is fed into a conventional oxidation reactor along with an oxygen source such as pure oxygen or, preferably, oxygen-enriched air. The system shown in FIGS. 4 and 5 utilizes pure oxygen as a feed. In the event that an oxygen-enriched stream is recycled from the PSA system to the reactor, it may be introduced independently or in combination with the oxygen feed. The relative proportions of each can be adjusted to achieve the desired amount of oxygen in the reactor. In the event that the feed to the oxidation reactor is oxygen-enriched air, the oxygen-containing stream produced by the PSA system may be vented or only partially recycled to the reactor. The amount of the oxygen-enriched stream produced by the PSA system which is vented will depend on the oxygen content of the reactor feed and the desired reactor pressure The venting of the oxygen-enriched stream through a purge line, not shown, thereby prevents the accumulation of nitrogen in the system. These considerations apply as well to the system shown in FIGS. 6 and 7 which is also illustrated with a pure oxygen feed.

The oxidation reactor utilized in the present process is conventional and may employ either a fixed, fluidized or slurry reactor and appropriate catalyst. The reaction may be carried out either in gas or liquid phase. If it is carried out in a liquid phase, a suitable solvent may also be employed. The reactor may contain a suitable oxidation catalyst such as silver oxide, molybdenum oxide, rhethenium oxide, or lanthanum oxide, alone or in combination with others, and they may be supported or unsupported. Various catalysts are disclosed, for example, in Fenton. U.S. Pat. No. 3,316,279, Waddan et al., European Patent Appln. No. 0 043 192, Bryce Smith, Great Britain Patent 1,409,421, Bobolev, Great Britain Patent Nos. 1,433,885, and 1,433,886, Kolombos et al., U.S. Pat. No. 3,888,889. Additional suitable catalysts are known to those skilled in the art.

The oxidation reaction is conducted at a temperature of from about 100 to 500° C., preferably from about 150° to 350° C.; at a pressure typically in the range of from about 10 to 1000 psig, preferably from about 150 to 750 psig. The reactor residence times vary depending upon the catalyst, as is well known to those skilled in the art, and it can be anywhere from a few seconds up to 1 hour. The oxygen-containing gas feed may be pure oxygen or oxygen-enriched air. In accordance with this invention, oxygen-enriched air preferably contains from about 30 to about 80, most preferably from about 55 to 65, percent by volume of oxygen. Such mixtures may be produced by adjusting the capacity of a conventional oxygen-producing unit, e.g. a conventional PSA system, or by mixing pure oxygen with air in the proper proportions. The ratio of oxygen to propylene in the feed converted to products is suitably in the range of from about 0.8:1 to 2.0:1 by volume.

The effluent from the oxidation reactor comprises a major amount of propylene oxide and minor amounts of acetone, acetaldehyde, formaldehyde, carbon oxides and nitrogen, when present in the feed, as well as unreacted oxygen, propylene and propane. This gaseous mixture is quenched or scrubbed with a liquid, such as water, to dissolve the water-soluble compounds for subsequent separation and recovery of the desired compounds.

The gas phase effluent from the quench step is introduced into a separator, e.g., a membrane, an absorber, a pressure swing adsorber (PSA) or a cryogenic setup. These separators can be used alone or in combination depending on whether pure oxygen or enriched air is utilized as the feed as is well known to those skilled in the art. For example, if enriched air is used as the feed, a membrane followed or preceded by a PSA can be used to prevent any nitrogen accumulation For purpose of the following illustration, a PSA system will be used. As used herein, a PSA system consists of two or more units in series, each unit comprising one or more adsorptive beds in parallel. PSA generally refers to a unit.

PSA is a well known process for separating the components of a mixture of gases by virtue of the difference in the degree of adsorption among them on a particular adsorbent retained in a stationary bed. Typically, two or more such beds are operated in parallel, as a cyclic process, comprising adsorption under relatively high pressure and desorption or bed regeneration under low pressure or vacuum. The desired component or components may be obtained during either of these stages. The cycle may contain other steps in addition to the fundamental steps of adsorption and regeneration, and it is commonplace to have two or more adsorbent beds cycled out of phase to assure a pseudo continuous flow of desired product. It is preferred to pass the quench tower effluent through a conventional dryer (not shown) to remove moisture therefrom prior to introducing it into the PSA.

It may be necessary to raise the pressure of the quench tower effluent in a compressor or other suitable means prior to introducing it into the PSA system. The compressor increases the pressure of the quench tower gaseous effluent to the operating pressure of a PSA system, typically from about 3 to 50 psig, preferably from about 20 to 40 psig. These ranges may vary to an extent depending on the adsorbent in the PSA system. It may also be necessary to pass the effluent through a conventional dryer (not shown) prior to introduction into the PSA system.

The PSA system utilized in accordance with the present invention comprises at least two adsorptive beds functioning in series. Of course, these beds in series may be physically located as discrete layers within a single vessel. The quench tower effluent entering the PSA system consists of propane, propylene, light hydrocarbons, i.e. ethane, ethylene and methane, as well as carbon monoxide, carbon dioxide, hydrogen, oxygen and nitrogen, if present in the feed. The adsorbent in the first bed can be any art-recognized material which will adsorb $C_3$ hydrocarbons preferentially to the other gases to produce an adsorbed stream containing alkane, alkene, minor quantities of oxygen and nitrogen, when present. Silica gel and activated carbon are preferred adsorbent materials. Silica gel is a particularly preferred material when oxygen-enriched air is utilized as a reactor feed material. An unadsorbed stream containing hydrogen, oxygen and nitrogen, if present, flowing through the first bed is introduced into the second bed.

The PSA system is operated such that the nonadsorbed stream flowing through the first bed is not flammable. In the next step of the PSA cycle, the pressure in the first bed is lowered to a value such that a waste stream, which contains the remaining light hydrocarbons and carbon dioxide, can be withdrawn from the outlet of the bed with minimal desorption of hydrocarbons. The waste stream may be either vented or incinerated. The adsorbed hydrocarbon recycle stream is then produced conventionally at the PSA inlet by desorbing the bed, and is utilized for recycle.

The adsorbent in the second bed of the PSA system is selected so that it will adsorb oxygen, and nitrogen if present, in preference to hydrogen to form an oxygen-enriched stream upon desorption. For example, a molecular sieve zeolite may be used. The second bed is operated in such a manner that the oxygen in the nonadsorbed effluent flowing therethrough is below flammability levels. The second bed produces a recycle stream of predominately oxygen and nitrogen when present, and a stream rich in hydrogen. The latter stream may be vented, taken as product or recycled to the dehydrogenator to maintain a desired level of hydrogen therein The PSA system is operated in a manner such that none of the streams produced thereby is flammable and the concentration of oxygen and hydrogen in their respective streams is maximized. For example, flammability of the oxygen-containing stream is suppressed by withdrawing it fuel-rich, i.e. containing a high percentage of hydrogen and light hydrocarbons.

Since the hydrogen-rich stream produced in the PSA system may contain some oxygen, it is not introduced directly into the dehydrogenator, but is instead introduced into the selective oxidation reactor with the hydrocarbon recycle stream. The amount of hydrogen required in the recycle feed to the dehydrogenator or the selective oxidator will vary with the catalyst and can be determined by operation of the system utilizing a given catalyst.

In the event that the feed to the oxidation reactor is pure oxygen, the PSA system produces an oxygen-enriched stream of product quality which is recycled to the reactor. As the percentage of nitrogen in the reactor feed increases, however, the amount of the oxygen stream that is recycled decreases to prevent the accumulation of nitrogen in the system. Even in the event that the oxygen-containing stream produced in the PSA system is totally purged, the process of the invention is advantageous in that oxygen loss is minimal and nitrogen build-up is prevented without the loss of an appreciable amount of reactant hydrocarbons.

While it is preferred that the two adsorbent beds in the PSA system be contained in separate vessels, it is within the scope of the present invention to utilize two discrete layers of adsorbent in a single vessel configured to provide the streams as described herein. In such a two layered vessel, for example, the waste stream containing light hydrocarbons and carbon oxides would be withdrawn from an intermediate level of the vessel without passing through the second layer.

The PSA recycle stream withdrawn from the first bed of the PSA system and introduced into the selective oxidation reactor contains propane, propylene, a minor quantity of oxygen, typically about 1-2 percent by volume, and nitrogen, if present in the feed. The selective oxidation reactor is of conventional configuration and contains an art-recognized catalyst capable of selectively catalyzing the reaction of oxygen and hydrogen to form water, i.e. the oxidation of hydrogen, without causing oxidation of the desired hydrocarbons, i.e. propane and propylene in the PSA effluent. Such catalysts and their use are well known. Suitable catalysts include noble metals or base metals, particularly platinum or palladium on alumina.

As previously stated, the selective oxidation reactor utilized in the embodiment of the present process shown in FIG. 4 requires only a modest capital expenditure in comparison with the multiple bed unit contemplated in the process illustrated in FIG. 3 since the PSA effluent in the subject process contains about 1-2 percent by volume of oxygen. Typically, the oxygen content of the PSA effluent in the present process is on the order of from about 0.01 to 1 percent by volume. Since the oxygen content is at such a low level, a small oxidation reactor consisting of a single bed without the need for catalyst regeneration over a period of several years is more than adequate in the method of this invention.

The effluent from the selective oxidation reactor, predominately propane and propylene, is recycled to the dehydrogenator. In the embodiment shown in FIG. 4, this recycle stream is combined with fresh feed and admitted to the dehydrogenator. In an alternative embodiment of the subject invention, the recycle stream is introduced into the latter stage of a multistage dehydrogenator as will be discussed hereafter.

The oxygen-containing stream produced by the PSA system of this invention generally contains from about 60 to about 95 percent of the unreacted oxygen in the quench tower effluent, depending on the amount of nitrogen present. The fact that the process of this invention provides an oxygen-containing stream is advantageous for two reasons. First, the PSA system effectively removes all but less than about one percent of the oxygen present in the quench tower effluent stream. Therefore, little is required to remove the rest as described above. Second, by returning such a high percentage of unreacted oxygen to the oxidation reactor, the PSA process of this invention significantly increases the overall efficiency of the process when the feed to the reactor contains a high percentage of oxygen. These benefits are realized by all embodiments of the present invention.

Figure 5:
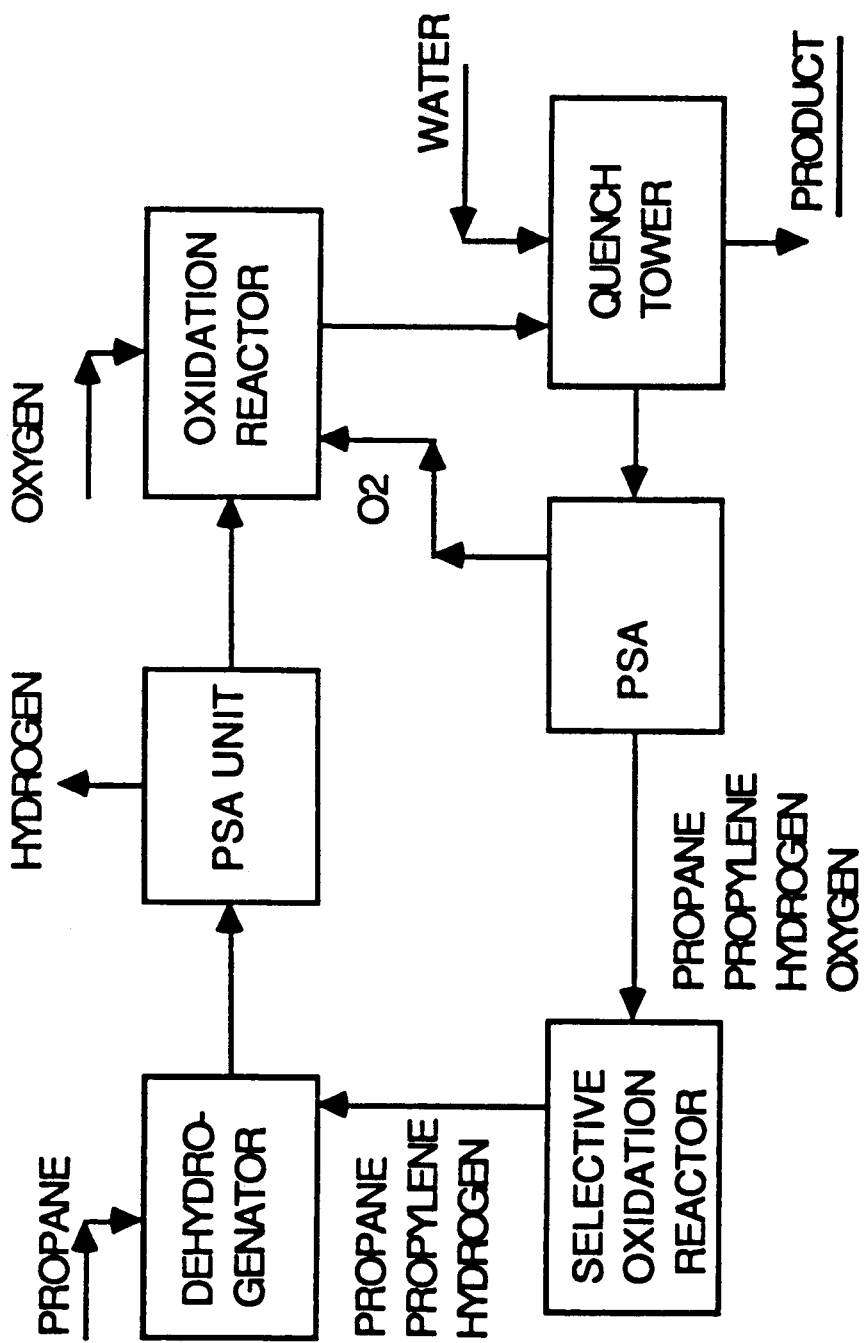
FIG. 5 illustrates in a block diagram the process of FIG. 4 wherein an additional PSA system removes hydrogen from the dehydrogenator effluent.

In the embodiment of the present invention illustrated in FIG. 5, a second PSA system is added to the process shown in FIG. 4. This second PSA system is located between the dehydrogenator and the oxidation reactor. Although the process shown in FIG. 5 is a modification of that shown in FIG. 4, a second PSA system may likewise be added to the system illustrated in FIG. 6 to function in a like manner. The second PSA system present in the process illustrated in FIG. 5 contains as adsorbent, such as silica gel or activated carbon, which will strongly adsorb C3 hydrocarbons and permit hydrogen to pass through. The resulting hydrogen-enriched stream may be vented or partially recycled as described herein, i.e., to the selective oxidation reactor or the dehydrogenator. When the optional second PSA system is present in the system, the novel PSA system of the present invention will not produce a hydrogen-enriched stream.

Figure 6:
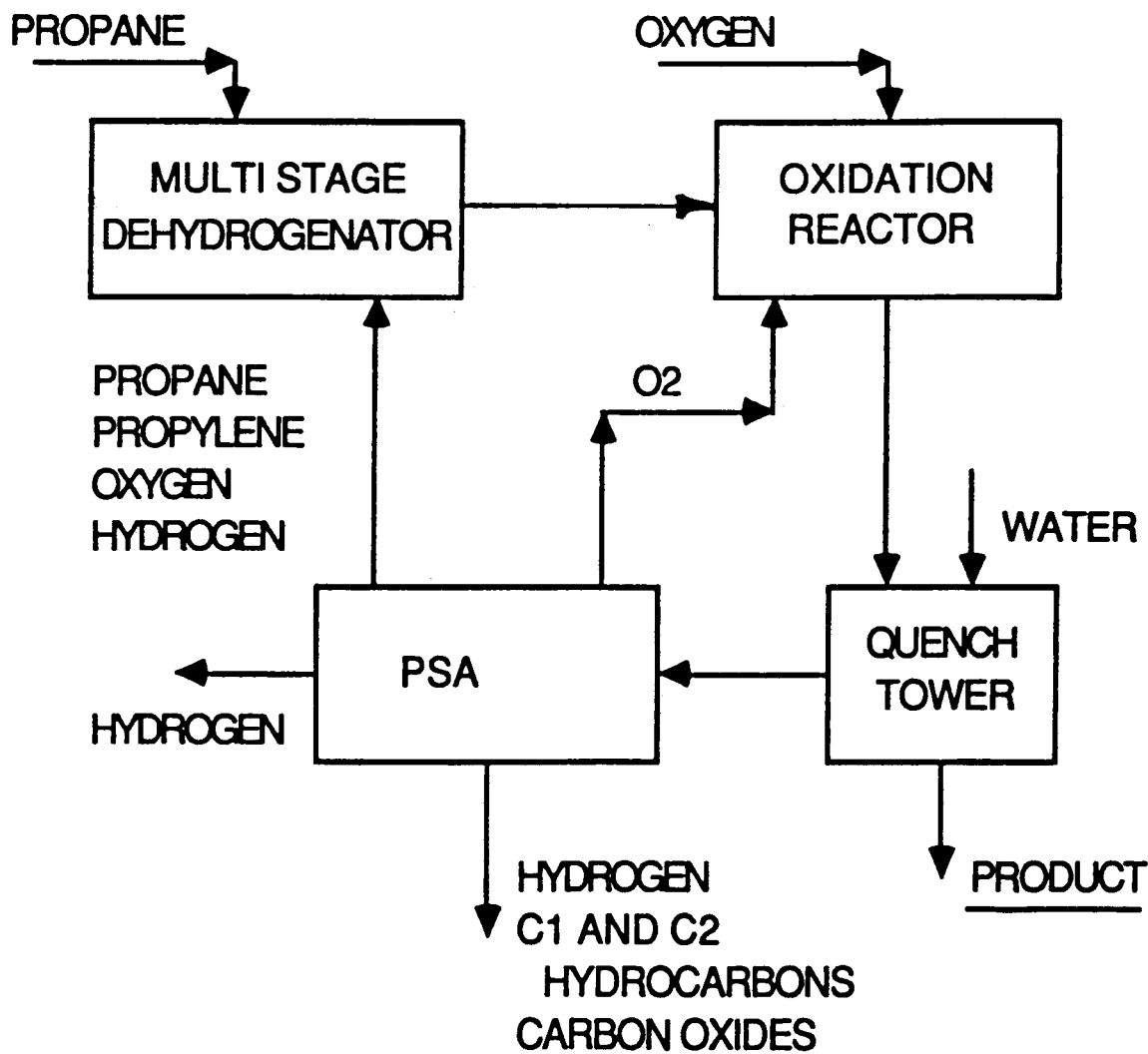
FIG. 6 illustrates in a block diagram the improvement of the present invention in a process for producing propylene oxide utilizing a multistage dehydrogenator without a selective oxidation unit downstream of the PSA system.

Turning to FIG. 6, the dehydrogenator utilized is a multistage unit which eliminates the need for the selective oxidation reactor. The use of a multistage catalytic reactor is described in the literature, e.g. Pujado et al., "Catalytic Conversion of LPG" presented at the American Institute of Chemical Engineers meeting at New Orleans, La. on April 6-10, 1986. In such reactors, the catalyst sequentially flows through a series of discrete reactors and is withdrawn at the end for regeneration and recycle. The reactant gas stream likewise flows through the reactors and is withdrawn into a heating means between each of the individual reactors. The dehydrogenator typically operates at a temperature of from about 500° to 800° C., preferably from about 600° to 700° C. The reheating of the reactant stream as it flows through the reactors is especially beneficial for an endothermic reaction such as the conversion of propane to propylene.

In the multistage dehydrogenator shown in FIG. 6, the reactant gas stream does not flow through all of the reactors, but is withdrawn as a product stream intermediate the first and last reactors. Preferably, there are at least four reactors and the product stream is withdrawn from the penultimate reactor. It is beneficial to withdraw the product stream from a latter stage of the dehydrogenator to obtain maximum efficiency therefrom. The reheating of the reactor stream takes place only up to and including the reactor from which the product stream is withdrawn.

The recycle stream from the PSA system of the present invention, which is comprised of unreacted alkane and alkene and a minor amount of oxygen, is introduced into the reactor following that from which the product stream is withdrawn, passed therethrough and through subsequent reactors, if any. The low oxygen content thereof can be eliminated without detriment to the system. Therefore, the selective oxidator present in the embodiments of the present invention shown in FIGS. 4 and 5 can be eliminated. The hydrogen-enriched stream produced in the PSA system may be introduced into the dehydrogenator, taken as product, or vented. The detail of the multistage dehydrogenator utilized in accordance with the present invention is shown in FIG. 7.

Figure 7:
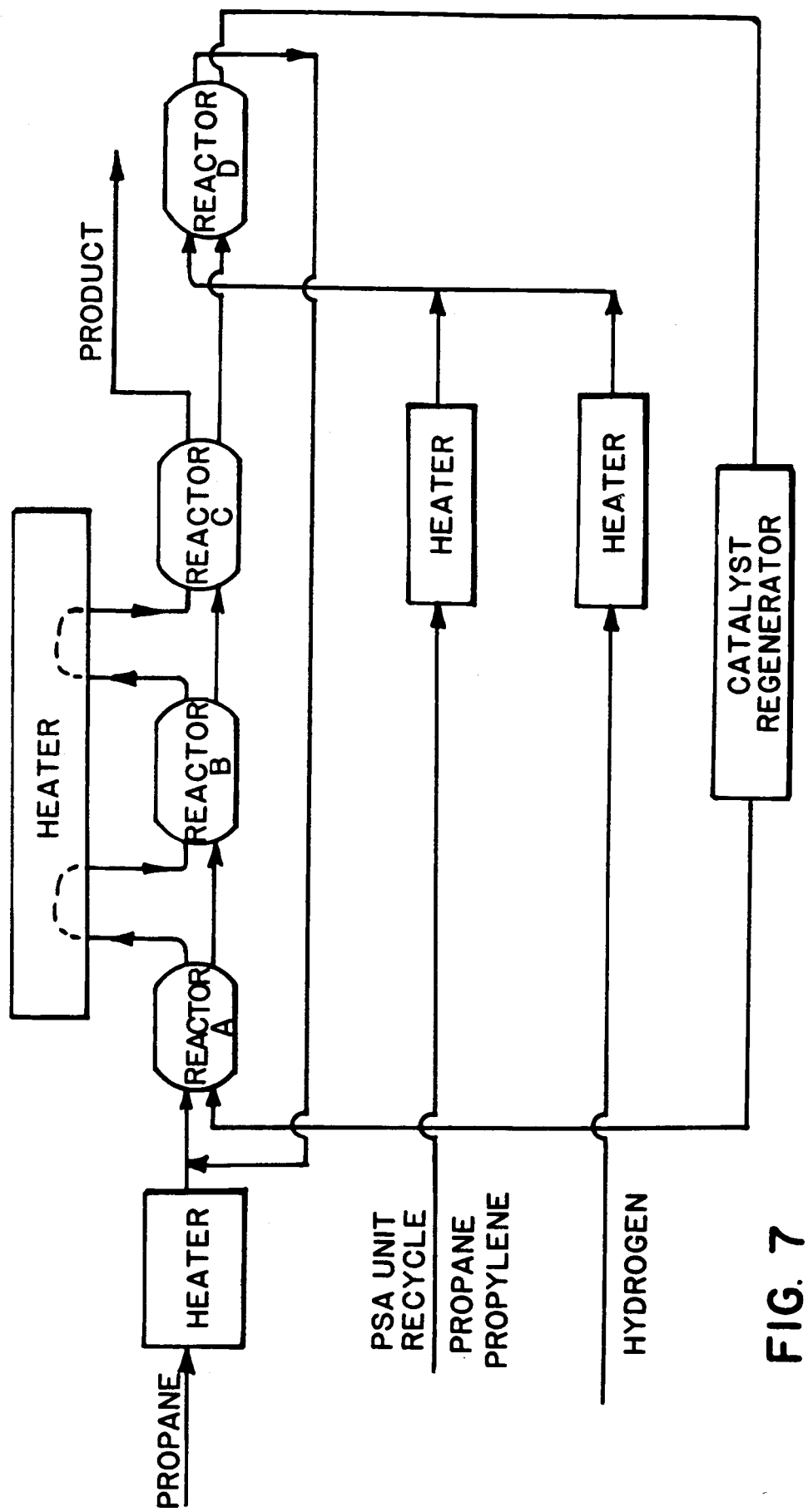
FIG. 7 illustrates in a block diagram detail of the multistage dehydrogenator shown in FIG. 6.

In the embodiment shown in FIG. 7, the effluent from the final reactor of the dehydrogenator is introduced into the initial feed stream. In the event that the feed to one of the intermediate reactors more closely approximates the effluent in regard to the concentration of the alkene than the initial feed, the effluent is introduced into such intermediate reactor. It is further contemplated to introduce the effluent from the final reactor directly into the oxidation reactor if the alkene content thereof is sufficiently high. This might occur, for example, when the PSA effluent passes through two or more reactors of the dehydrogenator.

The hydrocarbon recycle stream from the PSA system of this invention contains practically no hydrogen. Therefore, a portion of the hydrogen stream produced by the PSA system may be combined with the hydrocarbon recycle stream and reintroduced into the multistage dehydrogenerator. A portion of the hydrogen stream can likewise be introduced into the initial feed to the multistage dehydrogenator to prolong the life of the catalyst therein.

It is contemplated herein, although not necessary, to add a second PSA system on the effluent from the dehydrogenator to remove hydrogen therefrom. The hydrogen thus obtained may be vented, recycled to the dehydrogenator feed or supplied to the heater in combination with an oxygen feed for combustion. As in the embodiment shown in FIG. 5, the first PSA system will not produce a hydrogen-enriched stream when the second PSA system is present. It will be appreciated by those skilled in the art that a single heater can be utilized in FIG. 7 with all streams flowing therethrough.

Utilizing a system as shown in FIG. 4 for the production of propylene oxide utilizing propane as the starting material, the total flow rates in moles at various points in the system were determined and are presented in Table I. The individual flow rates are expressed in mole percent based on 100 moles of propylene oxide produced. The propane feed was virtually 100 percent propane and the feed to the oxidation reactor was pure oxygen. The data expressed in Table I represents operation of the system under conditions such that 20 percent of the propylene in the feed to the oxidation reactor is converted to different products, including propylene oxide (PO), in the oxidation reactor.

In Table I, Point A is the feed into the dehydrogenator after the stream from the selective oxidation reactor has been combined with fresh propane, Point B is the combined feed into the oxidation reactor, Point C is the oxidation reactor effluent, Point D is the quench tower gaseous effluent to the PSA system, Point E is the hydrocarbon-rich recycle stream from the PSA system and Point F is the oxygen-enriched recycle from the PSA system. As previously mentioned, the amount of hydrogen in the feed to the dehydrogenator will vary with the catalyst and reaction conditions used, and may be negligible. For purposes of the comparative results given in Tables I, II, III, IV, V and VI, the hydrogen to propane ratio in the dehydrogenator feed, Point A, was kept at about 0.5.

TABLE I

| | 20 Percent Conversion - Pure Oxygen Feed | | | | | |
|---|---|---|---|---|---|---|
| Component | A % | B % | C % | D % | E % | F % |
| $C_3H_6$ | 38.0 | 33.1 | 30.8 | 35.4 | 59.3 | 8.0 |
| $C_3H_8$ | 37.9 | 14.6 | 16.9 | 19.5 | 32.6 | 4.4 |
| $O_2$ | 0.7 | 23.5 | 4.0 | 5.7 | 1.0 | 34.4 |
| PO | | | 5.4 | | | |
| Acetone | | | 0.5 | | | |
| $C_2H_5COOH$ | | | 0.3 | | | |
| HCHO | | | 0.5 | | | |
| $CH_3CHO$ | | | 0.2 | | | |
| CO | 0.1 | 0.3 | 0.8 | 0.5 | 0.1 | 3.2 |
| $CO_2$ | 3.3 | 2.4 | 6.3 | 4.0 | 5.1 | 4.5 |
| $H_2O$ | | | 3.9 | | | |
| $CH_4$ | 0.2 | 1.4 | 1.6 | 1.8 | 0.3 | 11.0 |
| $C_2H_4$ | 0.1 | 0.3 | 0.4 | 0.5 | 0.1 | 2.7 |
| $C_2H_6$ | 0.3 | 1.7 | 2.0 | 2.3 | 0.4 | 13.7 |
| $H_2$ | 19.6 | 22.7 | 26.4 | 30.4 | 1.1 | 18.2 |
| $N_2$ | | | | | | |
| TOTAL (moles) | 1383.8 | 2158.9 | 1856.4 | 1615.7 | 887.2 | 166.0 |

Again utilizing a system as shown in FIG. 4 for the production of propylene oxide with propane as a starting material, the oxygen feed to the oxidation reactor was changed to an equal mixture of pure oxygen and air which produced oxygen-enriched air containing approximately 60 percent by volume of oxygen. The flow rates at various points in the system were determined and are presented in Table II. The data expressed in Table II represents operation of the system under conditions such that 20 percent of the propylene in the feed to the oxidation reactor is converted therein to different products, including propylene oxide.

TABLE II

| | 20 Percent Conversion - Equal Parts Pure Oxygen and Air | | | | | |
|---|---|---|---|---|---|---|
| Component | A % | B % | C % | D % | E % | F % |
| $C_3H_6$ | 35.2 | 21.9 | 10.3 | 20.0 | 52.6 | 1.5 |
| $C_3H_8$ | 35.0 | 9.6 | 10.6 | 11.5 | 29.0 | 0.9 |
| $O_2$ | 1.0 | 16.9 | 4.0 | 5.4 | 1.5 | 10.7 |
| PO | | | 3.4 | | | |
| Acetone | | | 0.3 | | | |
| $C_2H_5COOH$ | | | 0.2 | | | |
| HCHO | | | 0.3 | | | |
| $CH_3CHO$ | | | 0.1 | | | |
| CO | 0.1 | 0.2 | 0.5 | 0.3 | 0.1 | 0.6 |
| $CO_2$ | 3.0 | 1.6 | 3.9 | 2.4 | 4.5 | 0.9 |
| $H_2O$ | | | 2.5 | | | |
| $CH_4$ | 0.2 | 0.9 | 1.0 | 1.1 | 0.3 | 2.1 |
| $C_2H_4$ | 0.0 | 0.2 | 0.2 | 0.3 | 0.1 | 0.5 |
| $C_2H_6$ | 0.2 | 1.1 | 1.2 | 1.4 | 0.4 | 2.7 |
| $H_2$ | 18.2 | 15.0 | 16.6 | 18.0 | 1.0 | 3.5 |
| $N_2$ | 7.1 | 32.5 | 35.8 | 38.8 | 10.6 | 76.5 |
| TOTAL (moles) | 1495.1 | 3261.5 | 2959.0 | 2729.3 | 998.5 | 852.0 |

Utilizing a system as shown in FIG. 5 for the production of propylene oxide using propane as the starting material, the flow rates at various points in the system are presented in Table III. The propane and pure oxygen feeds were as in Table I. The system was operated to convert 20 percent of the propylene feed to the oxidation reactor to products.

In Table III, Point A is the feed into the dehydrogenator after the recycle stream has been combined therewith, Point B is the total feed into the oxidation reactor, Point C is the oxidation reactor effluent, Point D is the quench tower gaseous effluent, Point E is the hydrocarbon-rich recycle stream to the selective oxidation reactor, and Point F is the oxygen-containing gas recycle from the PSA system.

TABLE III

| | 20 Percent Conversion - Equal Parts Pure Oxygen and Air | | | | | |
|---|---|---|---|---|---|---|
| Component | A % | B % | C % | D % | E % | F % |
| $C_3H_6$ | 35.5 | 25.5 | 22.9 | 25.2 | 53.5 | 1.6 |
| $C_3H_8$ | 35.0 | 9.6 | 10.6 | 11.5 | 29.0 | 0.9 |
| $O_2$ | 0.8 | 19.0 | 4.0 | 5.5 | 1.3 | 9.6 |
| PO | | | 4.0 | | | |
| Acetone | | | 0.3 | | | |
| $C_2H_5COOH$ | | | 0.3 | | | |
| HCHO | | | 0.3 | | | |
| $CH_3CHO$ | | | 0.2 | | | |
| CO | 0.1 | 0.2 | 0.6 | 0.4 | 0.1 | 0.7 |
| $CO_2$ | 3.0 | 1.9 | 4.7 | 2.8 | 4.6 | 0.9 |
| $H_2O$ | | | 2.9 | | | |
| $CH_4$ | 0.2 | 1.0 | 1.1 | 1.3 | 0.3 | 2.2 |
| $C_2H_4$ | 0.0 | 0.3 | 0.3 | 0.3 | 0.1 | 0.6 |
| $C_2H_6$ | 0.2 | 1.3 | 1.4 | 1.6 | 0.4 | 2.8 |
| $H_2$ | 17.8 | 2.6 | 2.9 | 3.2 | 0.1 | 0.6 |
| $N_2$ | 7.0 | 37.2 | 41.7 | 46.0 | 10.6 | 80.2 |
| TOTAL (moles) | 1482.6 | 2802.8 | 2499.7 | 2265.9 | 983.1 | 800.3 |

TABLE IV

| | 20 Percent Conversion - Pure Oxygen Feed | | | | | |
|---|---|---|---|---|---|---|
| Component | A % | B % | C % | D % | E % | F % |
| $C_3H_6$ | 38.3 | 41.6 | 40.4 | 48.8 | 60.2 | 10.5 |
| $C_3H_8$ | 38.2 | 18.1 | 22.0 | 26.6 | 32.8 | 5.7 |
| $O_2$ | 0.5 | 28.5 | 4.0 | 6.0 | 0.8 | 34.8 |
| PO | | | 7.1 | | | |
| Acetone | | | 0.6 | | | |
| $C_2H_5COOH$ | | | 0.5 | | | |
| HCHO | | | 0.6 | | | |
| $CH_3CHO$ | | | 0.3 | | | |
| CO | 0.1 | 0.4 | 1.0 | 0.7 | 0.1 | 4.2 |
| $CO_2$ | 3.3 | 3.0 | 8.2 | 5.5 | 5.2 | 5.9 |
| $H_2O$ | | | 5.1 | | | |

TABLE IV-continued

| | 20 Percent Conversion - Pure Oxygen Feed | | | | | |
|---|---|---|---|---|---|---|
| Component | A % | B % | C % | D % | E % | F % |
| $CH_4$ | 0.2 | 1.7 | 2.0 | 2.5 | 0.3 | 14.1 |
| $C_2H_4$ | 0.1 | 0.4 | 0.5 | 0.6 | 0.1 | 3.5 |
| $C_2H_6$ | 0.3 | 2.1 | 2.5 | 3.1 | 0.4 | 17.6 |
| $H_2$ | 19.2 | 4.2 | 5.1 | 6.2 | 0.2 | 3.6 |
| $N_2$ | | | | | | |
| TOTAL (moles) | 1373.0 | 1717.4 | 1414.9 | 1170.2 | 873.5 | 125.3 |

The system shown in FIG. 5 was utilized for the production of propylene oxide with propane as the starting material and utilizing an equal mixture of pure oxygen and air is shown in Table II. The results are repeated in Table IV, again operating the system to produce propylene oxide at 20 percent conversion of the propylene in the feed to products.

For the system shown in FIG. 4, Tables V and VI detail the compositions for combination absorber-PSA and membrane-PSA separators, respectively, in the production of propylene oxide. In Table V, point A is the combined feed to the dehydrogenator, B is the combined feed to oxidation reactor, C is the oxidation reactor effluent, D is the quench tower effluent, E is the hydrocarbon stream from the absorber, F is the hydrogen-enriched stream, and G is the oxygen-enriched stream. In Table VI, point A is the combined feed to the dehydrogenator, B is the combined feed to the oxidation reactor, C is the oxidation reactor effluent, D is the quench tower gaseous effluent, E is the hydrogen-enriched stream from the membrane, F is the hydrocarbon-rich recycle stream, and G is the oxygen-enriched recycle stream.

TABLE V

| | 20 Percent Conversion - Pure Oxygen Feed; Absorber-PSA Separator | | | | | | |
|---|---|---|---|---|---|---|---|
| Component | A % | B % | C % | D % | E % | F % | G % |
| $C_3H_6$ | 40.2 | 35.1 | 33.0 | 37.3 | 63.7 | 1.4 | 14.8 |
| $C_3H_8$ | 34.7 | 13.9 | 16.3 | 18.4 | 31.5 | 0.7 | 7.3 |
| $O_2$ | 0.0 | 24.7 | 4.0 | 4.5 | 0.3 | 2.4 | 28.8 |
| PO | | | 5.8 | | | | |
| Acetone | | | 0.5 | | | | |
| $C_2H_5COOH$ | | | 0.4 | | | | |
| HCHO | | | 0.5 | | | | |
| $CH_3CHO$ | | | 0.2 | | | | |
| CO | 0.3 | 1.2 | 0.7 | 0.8 | 0.0 | 0.5 | 5.4 |
| $CO_2$ | 1.7 | 1.2 | 5.1 | 5.8 | 1.4 | 1.6 | 9.5 |
| $H_2O$ | | | 4.2 | | | | |
| $CH_4$ | 1.8 | 1.6 | 1.9 | 2.2 | 0.2 | 3.2 | 8.7 |
| $C_2H_4$ | 0.7 | 0.6 | 0.7 | 0.7 | 0.4 | 0.8 | 2.2 |
| $C_2H_6$ | 3.3 | 2.8 | 3.3 | 3.7 | 2.0 | 4.0 | 10.8 |
| $H_2$ | 17.3 | 20.0 | 23.5 | 26.5 | 0.4 | 85.5 | 12.4 |
| $N_2$ | | | | | | | |
| TOTAL (moles) | 1356.5 | 2035.9 | 1733.4 | 1532.7 | 843.5 | 443.2 | 48.7 |

TABLE VI

| | 20 Percent Conversion - Pure Oxygen Feed; Membrane-PSA Separator | | | | | | |
|---|---|---|---|---|---|---|---|
| Component | A % | B % | C % | D % | E % | F % | G % |
| $C_3H_6$ | 37.7 | 33.4 | 31.1 | 35.6 | 1.8 | 59.8 | 9.5 |
| $C_3H_8$ | 38.8 | 15.1 | 17.6 | 20.1 | 1.0 | 33.7 | 5.4 |
| $O_2$ | 0.6 | 23.7 | 4.0 | 5.7 | 1.9 | 1.0 | 38.7 |
| PO | | | 5.5 | | | | |
| Acetone | | | 0.5 | | | | |
| $C_2H_5COOH$ | | | 0.4 | | | | |
| HCHO | | | 0.5 | | | | |
| $CH_3CHO$ | | | 0.2 | | | | |

TABLE VI-continued

| | 20 Percent Conversion - Pure Oxygen Feed; Membrane-PSA Separator | | | | | | |
|---|---|---|---|---|---|---|---|
| Component | A % | B % | C % | D % | E % | F % | G % |
| CO | 0.1 | 0.3 | 0.8 | 0.5 | 0.0 | 0.1 | 3.8 |
| $CO_2$ | 2.6 | 2.0 | 5.8 | 4.0 | 4.5 | 4.1 | 4.3 |
| $H_2O$ | | | 4.0 | | | | |
| $CH_4$ | 0.2 | 1.4 | 1.6 | 1.8 | 0.1 | 0.3 | 13.0 |
| $C_2H_4$ | 0.0 | 0.3 | 0.3 | 0.4 | 0.2 | 0.1 | 2.5 |
| $C_2H_6$ | 0.2 | 1.4 | 1.7 | 1.9 | 1.0 | 0.3 | 12.7 |
| $H_2$ | 19.7 | 22.5 | 26.2 | 29.9 | 89.5 | 0.5 | 10.1 |
| $N_2$ | | | | | | | |
| TOTAL (moles) | 1382.3 | 2137.1 | 1834.6 | 1604.2 | 285.4 | 871.0 | 137.3 |

The process of this invention is advantageous in that it is very efficient and is cost attractive in comparison to prior art processes. It is readily apparent from the data presented in Tables I, II, III, IV, V, and VI that the subject process has a comparatively small incidence of build-up of any of the components of the various gaseous streams formed or separated at any stage thereof. Further, the subject process can be utilized with air or an oxygen-enriched air feed, heretofore not feasible with a closed loop system. Unexpectedly, the subject process operates at particularly enhanced efficiency with an oxygen-enriched air feed.

The invention has been described with reference to preferred embodiments thereof. It will be appreciated by those skilled in the art that various modifications may be made from the specific details given without departing from the spirit and scope of the invention.

We claim:

1. In a process for the production of alkylene oxides comprising:
   (a) forming an alkene from a gaseous alkane in a catalytic dehydrogenator;
   (b) introducing a gaseous stream comprising said alkene and an oxygen source selected from the group consisting of pure oxygen or a gas enriched in oxygen relative to air into a suitable oxidation reactor and reacting them in the presence of an oxidation catalyst at about 100 to 500° C. 10 to 1000 psig, and a residence time from a few seconds up to 1 hour to produce a gaseous effluent containing said oxide;
   (c) quenching said effluent in a liquid to form a liquid phase containing said oxide and a gaseous phase;
   (d) recovering said oxide from said liquid phase;
   (e) introducing the gaseous phase under pressure into a separator to thereby form (i) a waste stream, (ii) an adsorbed stream comprising said unreacted alkane and alkene, a minor amount of oxygen, and nitrogen when oxygen-enriched air is introduced into the reactor as the oxygen source in step (b), (iii) and a hydrogen-enriched stream;
   (f) introducing said adsorbed stream into a catalytic selective oxidation unit to remove the remaining oxygen in said stream; and
   (g) recycling the effluent from the selective oxidation unit to the dehydrogenator, the improvement wherein the separator also forms a oxygen-enriched stream, with nitrogen when present, which is at least partially recycled to the oxidation reactor.

2. A process in accordance with claim 1, wherein the separator is a PSA system consisting of two or more units in series, each unit comprising one or more adsorptive beds in parallel, wherein the first unit preferentially adsorbs said alkane and alkene to other gases thereby forming the adsorbed stream and the waste stream, and wherein the remaining gaseous effluent of the first unit comprising oxygen, hydrogen and nitrogen, when present, is introduced into the second bed in series thereby forming the oxygen-enriched stream containing nitrogen, when present, and the hydrogen-enriched stream.

3. A process in accordance with claim 1, wherein the separator is a combination of membrane and PSA, the membrane preferentially separates hydrogen via a hydrogen-enriched stream, and the remaining gaseous effluent of the membrane system is introduced into the PSA which preferentially adsorbs said alkane and alkene to other gases thereby forming the adsorbed stream, the waste stream, and the oxygen-enriched stream with nitrogen, when present.

4. A process in accordance with claim 1, wherein the separator is a combination of PSA and membrane, the PSA preferentially adsorbs alkane and alkene to other gases thereby forming the adsorbed stream and the waste stream, and the remaining gaseous effluent of the PSA is introduced into the membrane thereby forming an oxygen-enriched stream with nitrogen, when present, and a hydrogen-enriched stream.

5. A process in accordance with claim 1, wherein the separator is a combination of absorber and PSA, the absorber produces a gaseous stream comprising unreacted alkane and alkene, a minor amount of oxygen and nitrogen, when present, and the remaining gaseous effluent of the absorber is introduced into the PSA thereby forming an oxygen-enriched stream with nitrogen, when present, a hydrogen-enriched stream, and a waste stream.

6. A process in accordance with claim 1, wherein the separator is a combination of absorber and PSA, the absorber produces a carbon dioxide-enriched stream and the remaining gaseous effluent of the absorber is introduced into the PSA thereby forming an adsorbed stream, an oxygen-enriched stream with nitrogen, when present, a hydrogen-enriched stream, and a waste stream.

7. A process in accordance with claim 1, wherein the separator is a combination of cryogenic setup and PSA, the cryogenic setup produces a gaseous stream comprising unreacted alkane and alkene, a minor amount of oxygen and nitrogen, when present, and the remaining gaseous effluent of the cryogenic setup is introduced into the PSA thereby forming an oxygen-enriched stream with nitrogen, when present, a hydrogen-enriched stream, and a waste stream.

8. A process in accordance with claim 1, wherein the recycled effluent from the selective oxidation unit is combined with fresh alkane feed before introduction into the dehydrogenator.

9. A process in accordance with claim 1, wherein the alkane is propane, the alkene is propylene and the alkylene oxide produced is propylene oxide.

10. A process in accordance with claim 3, wherein oxygen is added in step (b) as oxygen-enriched air containing from about 30 to about 80 percent of oxygen by volume.

11. A process in accordance with claim 1, wherein the portion of the oxygen-enriched stream with nitrogen not recycled is vented to prevent accumulation of nitrogen in the system.

12. A process in accordance with claim 2, wherein units may be combined such that the series of beds of the units are contained in a single vessel as discrete layers.

13. A process in accordance with claim 1, wherein at least a portion of the hydrogen-enriched stream is passed through the selective oxidation unit with the alkane and alkene-containing stream and recycled to the dehydrogenator.

14. A process in accordance with claim 1, wherein the effluent from the catalytic dehydrogenator is passed through a second separator to remove hydrogen therefrom prior to being introduced into the reactor in step (b).

15. A process in accordance with claim 14, wherein the hydrogen stream from the second separator is recycled to the dehydrogenator.

16. A process in accordance with claim 1, wherein the alkane is ethane, the alkene is ethylene and the alkylene oxide produced is ethylene oxide.

17. A process in accordance with claim 1, wherein the catalytic dehydrogenator is comprised of a series of at least three discrete catalytic reactors, the product stream containing said alkene and unreacted alkane is withdrawn from a reactor intermediate the first and last of said reactors, the gaseous flow between said reactors, including the reactor from which the product stream is withdrawn is passed through a heating means to raise the temperature thereof, the catalyst in the dehydrogenator is passed through all of said reactors regenerated and recycled to the first reactor, the recycle stream containing alkene, and unreacted alkane is passed directly from the separator to the reactors in the dehydrogenator which follow in sequence the reactor from which the, product stream was withdrawn thereby removing substantially all of the oxygen in said stream, and the effluent from said last reactor is introduced into the first reactor or a reactor other than the first reactor wherein the concentration of the alkene is approximately the same as that of said effluent or said reactor in step (b).

18. A process in accordance with claim 17, wherein the dehydrogenator contains at least four reactors and the product stream is withdrawn from the penultimate reactor.

19. A process in accordance with claim 17, wherein the effluent from said last reactor is introduced into the feed to said first reactor.

20. A process in accordance with claim 17, wherein the effluent from said last reactor is introduced into a reactor other than said first reactor wherein the concentration of the alkene is approximately the same as that of said effluent.

21. The process in accordance with claim 17, wherein the effluent from said last reactor is introduced into said reactor in step (b).

22. A process in accordance with claim 17, wherein the product stream withdrawn from the dehydrogenator is passed through a second separator to remove hydrogen therefrom prior to introduction into said reactor in step (b).

23. A process in accordance with claim 22, wherein the hydrogen-containing stream produced in the second separator is recycled to the dehydrogenator.

24. A process in accordance with claim 17, wherein the temperature in the dehydrogenator is from about 500° to 800° C.

25. A process in accordance with claim 17, wherein the alkane is propane, the alkene is propylene and the alkylene oxide produced is propylene oxide.

26. A process in accordance with claim 17, wherein the alkane is ethane, the alkene is ethylene, and the alkylene oxide produced is ethylene oxide.

27. In a process for the production of alkylene oxides comprising:
(a) forming an alkene from a gaseous alkane in a catalytic dehydrogenator;
(b) introducing a gaseous stream comprising said alkene and an oxygen source selected from the group consisting of pure oxygen or a gas enriched in oxygen relative to air into a suitable oxidation reactor and reacting them in the presence of an oxidation catalyst at about 100° to 500° C. 10 to 1000 psig, and a residence time from a few seconds up to 1 hour to produce a gaseous effluent containing said oxide;
(c) quenching said effluent in a liquid to form a liquid phase containing said oxide and a gaseous phase;
(d) recovering said oxide from said liquid phase;
(e) introducing the gaseous phase under pressure into a separator to thereby form (i) a waste stream, (ii) an adsorbed stream comprising said unreacted alkane and alkene, a minor amount of oxygen, and nitrogen when oxygen-enriched air is introduced into the reactor as the oxygen source in step (b), (iii) and a hydrogen-enriched stream;
(f) introducing said adsorbed stream into a catalytic selective oxidation unit to remove the remaining oxygen in said stream; and
(g) recycling the effluent from the selective oxidation unit to the dehydrogenator, the improvement wherein the separator also forms a oxygen-enriched stream, with nitrogen when present, which is at least partially recycled to the oxidation reactor.

* * * * *